(12) United States Patent
Henry (10) Patent No.: US 11,285,434 B2
(45) Date of Patent: Mar. 29, 2022

(54) MEMBRANE PROCESS AND SYSTEM FOR HIGH RECOVERY OF A NONPERMEATING GAS

(71) Applicant: Air Products and Chemicals, Inc., Allentown, PA (US)

(72) Inventor: Donald E. Henry, Allentown, PA (US)

(73) Assignee: Air Products and Chemicals, Inc., Allentown, PA (US)

(*) Notice: Subject to any disclaimer, the term of this patent is extended or adjusted under 35 U.S.C. 154(b) by 0 days.

(21) Appl. No.: 16/834,270

(22) Filed: Mar. 30, 2020

(65) Prior Publication Data
US 2021/0299605 A1 Sep. 30, 2021

(51) Int. Cl.
| | | |
|---|---|---|
| *B01D 53/22* | (2006.01) | |
| *C10L 3/10* | (2006.01) | |
| *C07C 7/00* | (2006.01) | |
| *C07C 7/144* | (2006.01) | |

(52) U.S. Cl.
CPC ............ *B01D 53/226* (2013.01); *C07C 7/005* (2013.01); *C07C 7/144* (2013.01); *C10L 3/104* (2013.01); *C10L 2290/548* (2013.01)

(58) Field of Classification Search
CPC .. B01D 53/22; C10L 3/10; C07C 7/00; C07C 7/144
See application file for complete search history.

(56) References Cited

U.S. PATENT DOCUMENTS

| | | | |
|---|---|---|---|
| 5,709,732 A | 1/1998 | Prasad | |
| 6,630,011 B1 * | 10/2003 | Baker | B01D 53/225 95/47 |
| 8,211,211 B1 * | 7/2012 | Knaebel | B01D 53/75 95/96 |
| 8,999,038 B2 * | 4/2015 | Ungerank | B01D 53/226 95/51 |

(Continued)

FOREIGN PATENT DOCUMENTS

| | | |
|---|---|---|
| EP | 0754487 | 1/1997 |
| EP | 2588217 | 2/2017 |

(Continued)

OTHER PUBLICATIONS

Rakesh Agrawal, et al., "Gas Separation Membrane Cascades Utilizing Limited Numbers of Compressors", AIChE Journal, vol. 42, 1996, p. 2141-2154.

*Primary Examiner* — Youngsul Jeong
(74) *Attorney, Agent, or Firm* — Amy Carr-Trexler (57) ABSTRACT

A method for separating a raw feed gas stream using a plurality of membrane separation stages includes separating a pressurized feed gas stream into a first nonpermeate stream and a first permeate stream, compressing the first permeate stream to form a compressed first permeate stream, separating the compressed first permeate stream into a second nonpermeate stream and a second permeate stream, separating the second permeate stream into a third nonpermeate stream and a third permeate stream, combining the third nonpermeate stream with a raw feed gas stream to form a (Continued)

combined feed stream, compressing the combined feed stream to form a compressed combined feed stream, and combining the second nonpermeate stream with the compressed combined feed stream to form the pressurized feed gas stream.

13 Claims, 6 Drawing Sheets

(56) References Cited

U.S. PATENT DOCUMENTS

| | | |
|---|---|---|
| 2007/0125537 A1 | 6/2007 | Lokhandwala et al. |
| 2013/0098242 A1 | 4/2013 | Ungerank et al. |
| 2017/0283292 A1* | 10/2017 | Kim ........................ C02F 11/04 |
| 2019/0224617 A1* | 7/2019 | Mitariten ................ C07C 7/005 |

FOREIGN PATENT DOCUMENTS

| | | |
|---|---|---|
| JP | 2018171596 | 11/2018 |
| WO | 2000016879 | 3/2000 |
| WO | 2020/203994 | 10/2020 |

\* cited by examiner

MEMBRANE PROCESS AND SYSTEM FOR HIGH RECOVERY OF A NONPERMEATING GAS

BACKGROUND

This application relates to a multi-stage membrane process and system for methane recovery from biogas.

Multi-stage cascaded designs such as those described in "Gas Separation Membrane Cascades Utilizing Limited Numbers of Compressors" by Agrawal and Xu in AIChE Journal (vol 42, 1996 p 2141) have been known in the art for over twenty years. However, these designs teach that every permeate stream must be compressed before it is fed to a subsequent membrane stage. Additionally, in prior cascaded designs, if a permeate stream was not recompressed, it was fed as a low pressure sweep gas to the permeate side of a subsequent membrane stage, and not as a high pressure feed gas.

Figure 5:
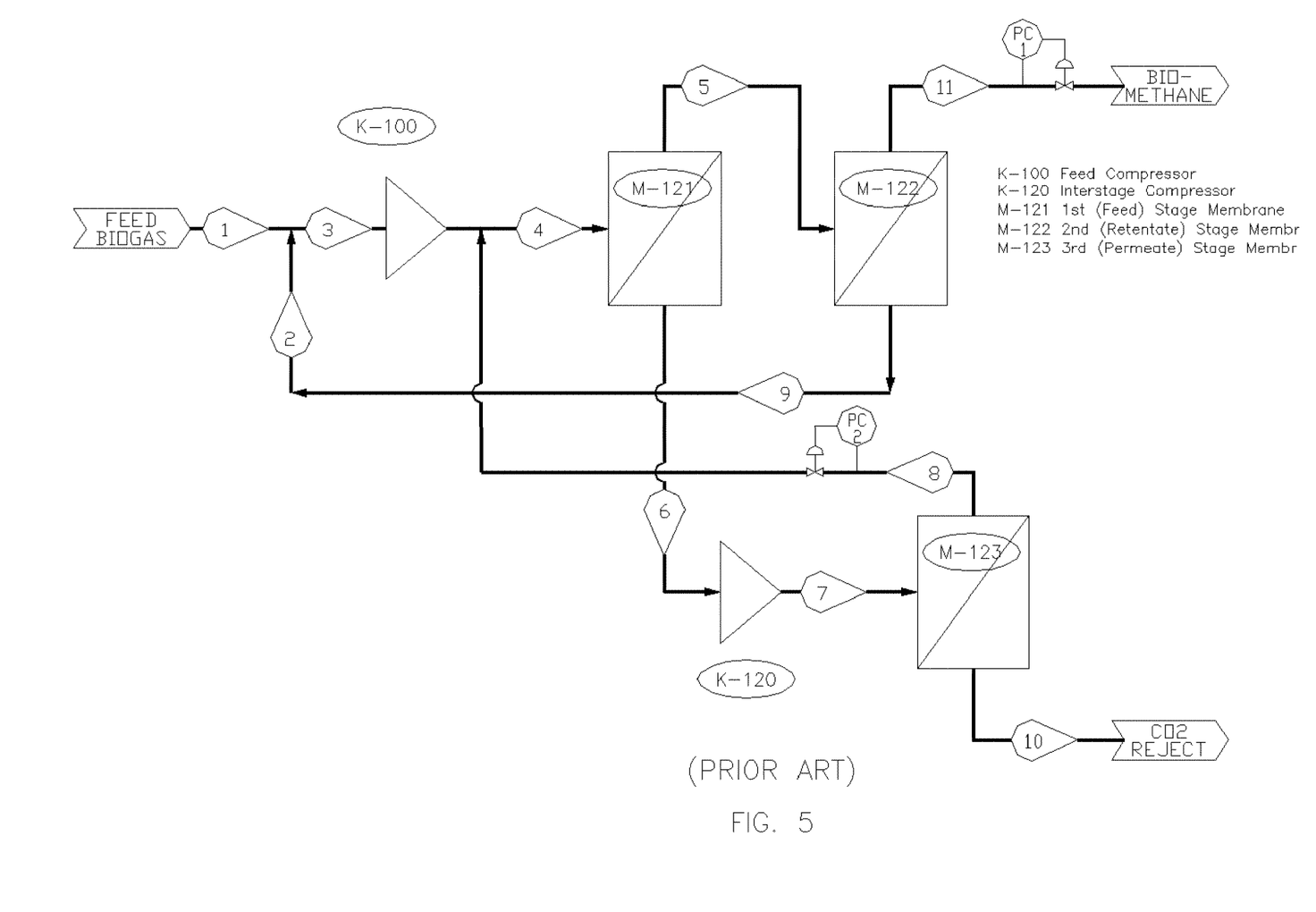
FIG. 5 is a process flow diagram of a prior art three-stage membrane system and process using two compressors.

In one prior art multi-stage membrane system, as illustrated in FIG. 5 (US 2019/0224617): a first membrane stage separates a feed stream (plus a recycle stream) to produce a first permeate stream and a first nonpermeate stream; a second membrane stage separates the first nonpermeate stream to produce a second nonpermeate stream (biomethane product) and a second permeate stream that is recycled back to the feed stream; a compressor compresses the first permeate stream which is then separated in a third membrane stage to produce a third permeate stream the exits the system and a third nonpermeate stream that is recycled back to the pressurized feed stream.

Figure 6:
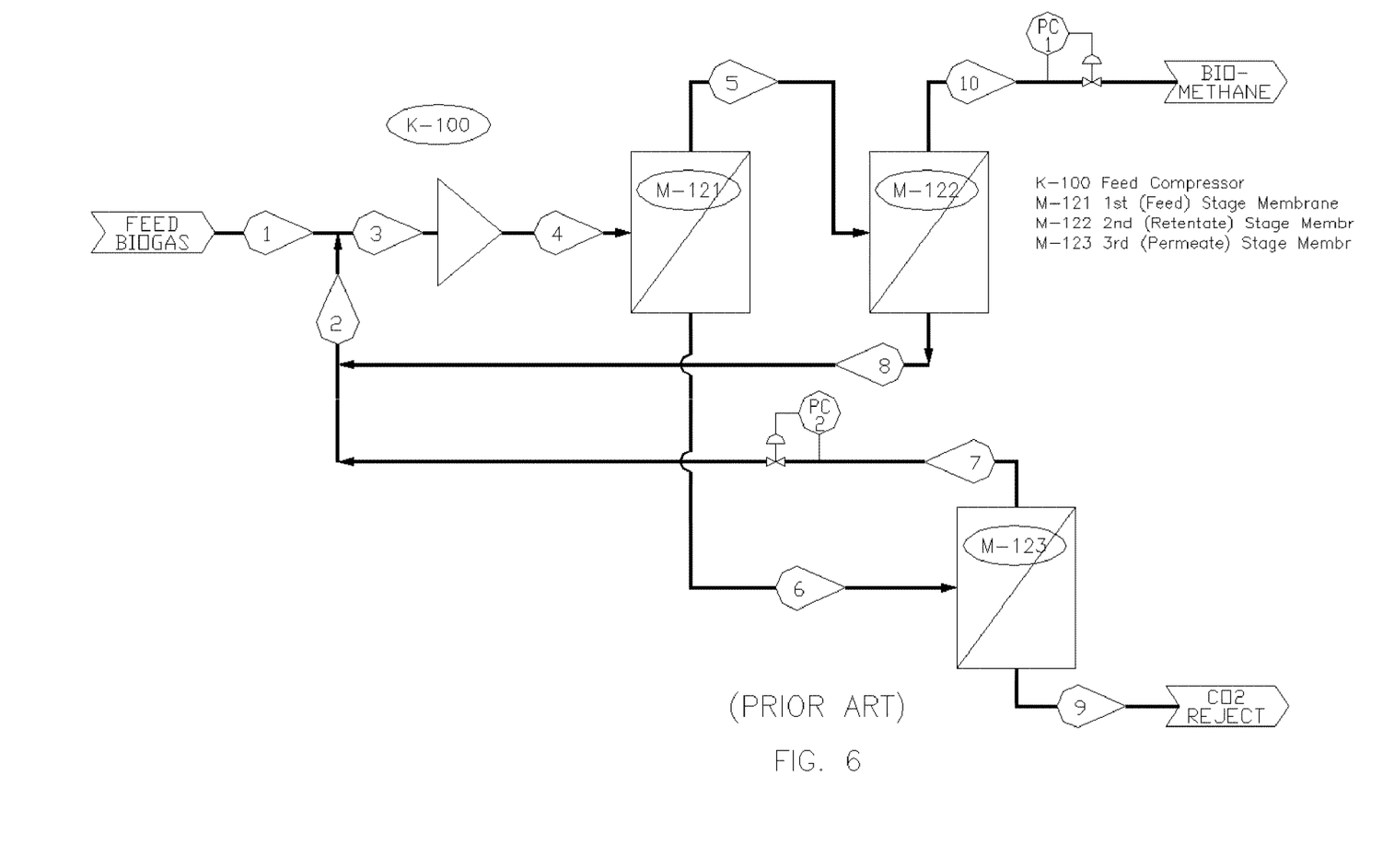
FIG. 6 is a process flow diagram of a prior art three-stage membrane system and process without recompression.

In another prior art multi-stage membrane system, as illustrated in FIG. 6 (EP 2588217), a three-stage membrane system is operated without recompression.

SUMMARY

In embodiments of the present invention, only the combined raw feed gas, which is at or near atmospheric pressure, plus the low pressure recycle stream (i.e., the third nonpermeate stream), and the permeate stream exiting the first membrane stage are compressed; and the permeate stream exiting the second membrane stage before it is fed to the third membrane stage is not compressed. Additionally, none of the permeate streams is used as a sweep gas.

Aspect 1. A method for separating a raw feed gas stream using a plurality of membrane separation stages, comprising: separating a pressurized feed gas stream into a first nonpermeate stream and a first permeate stream; compressing the first permeate stream to form a compressed first permeate stream; separating the compressed first permeate stream into a second nonpermeate stream and a second permeate stream; separating the second permeate stream into a third nonpermeate stream and a third permeate stream; combining the third nonpermeate stream with a raw feed gas stream to form a combined feed stream; compressing the combined feed stream to form a compressed combined feed stream; and combining the second nonpermeate stream with the compressed combined feed stream to form the pressurized feed gas stream.

Aspect 2. The method of aspect 1, further comprising: withdrawing the first nonpermeate stream as a product gas stream.

Aspect 3. The method of aspect 1 or aspect 2, further comprising: withdrawing the third permeate stream as a waste gas stream.

Aspect 4. The method of any one of aspects 1 to 3, further comprising: controlling the pressure of the first nonpermeate stream; and controlling the pressure of the third nonpermeate stream.

Aspect 5. The method of any one of aspects 1 to 4 1, further comprising: separating the first nonpermeate stream into a fourth nonpermeate stream and a fourth permeate stream; combining the fourth permeate stream with the third nonpermeate stream prior to combining the third nonpermeate stream with the raw feed gas stream to form the combined feed stream; and withdrawing the fourth nonpermeate stream as a product gas stream.

Aspect 6. The method of any one of aspects 1 to 5, further comprising: applying negative pressure to at least one of the first permeate stream and the third permeate stream.

Aspect 7. A multi-stage membrane system for separating a raw feed gas stream, comprising: a first membrane stage having a first feed port for receiving a pressurized raw feed gas stream, a first nonpermeate outlet for discharging a first nonpermeate stream, and a first permeate outlet for discharging a first permeate stream; an interstage compressor having an interstage compressor inlet operatively connected to the first permeate outlet to receive the first permeate stream and an interstage compressor outlet for discharging a compressed first permeate stream; a second membrane stage having a second feed port operatively connected to the interstage compressor outlet to receive the compressed first permeate stream, a second permeate outlet for discharging a second permeate stream, and a second nonpermeate outlet for discharging a second nonpermeate stream; a third membrane stage having a third feed port operatively connected to the second permeate outlet to receive the second permeate stream, a third permeate outlet for discharging a third permeate stream, and a third nonpermeate outlet for discharging a third nonpermeate stream; a first mixing junction having a raw feed gas inlet for receiving a raw feed gas stream, a first recycle inlet operatively connected to the third permeate outlet to receive the third permeate stream, and a first mixture outlet for discharging a combined feed stream consisting of a mixture of the raw feed gas stream and the third permeate stream; a feed compressor having a feed compressor inlet operatively connected to the first mixture outlet to receive the combined feed stream and a feed compressor outlet for discharging a compressed combined feed stream; and a second mixing junction having a combined feed inlet operatively connected to the feed compressor outlet to receive the compressed combined feed stream, a second recycle inlet operatively connected to the second nonpermeate outlet to receive the second nonpermeate stream, and a second mixture outlet operatively connected to the first feed port to supply the pressurized raw feed gas stream consisting of a mixture of the compressed combined feed stream and the second nonpermeate stream to the first membrane stage.

Aspect 8. The system of aspect 7, further comprising: a fourth membrane stage having a fourth feed port operatively connected to the first nonpermeate outlet to receive the first permeate stream, a fourth permeate outlet port for discharging a fourth permeate stream, and a fourth nonpermeate outlet for discharging a fourth nonpermeate stream; wherein the fourth permeate stream is combined with the third nonpermeate stream prior to the third nonpermeate stream being received into the first mixing junction.

Aspect 9. The system of aspect 7 or aspect 8, further comprising: a first permeate vacuum pump to apply negative pressure to the first permeate outlet.

Aspect 10. The system of any one of aspects 7 to 9, further comprising: a third permeate vacuum pump to apply negative pressure to the third permeate outlet.

Aspect 11. The system of any one of aspects 7 to 10, wherein the first membrane stage, the second membrane stage, and the third membrane stage each have membranes of the same permeability and selectivity.

Aspect 12. The system of any one of aspects 7 to 11, wherein one of the first membrane stage, the second membrane stage, and the third membrane stage has membranes of different permeability and selectivity that the other two stages.

Aspect 13. The system of any one of aspects 7 to 12, wherein each of the first membrane stage, the second membrane stage, and the third membrane stage has membranes of different permeability and selectivity each of the other stages.

The various aspects of the system disclosed herein can be used alone or in combinations with each other.

DETAILED DESCRIPTION

Figure 1:
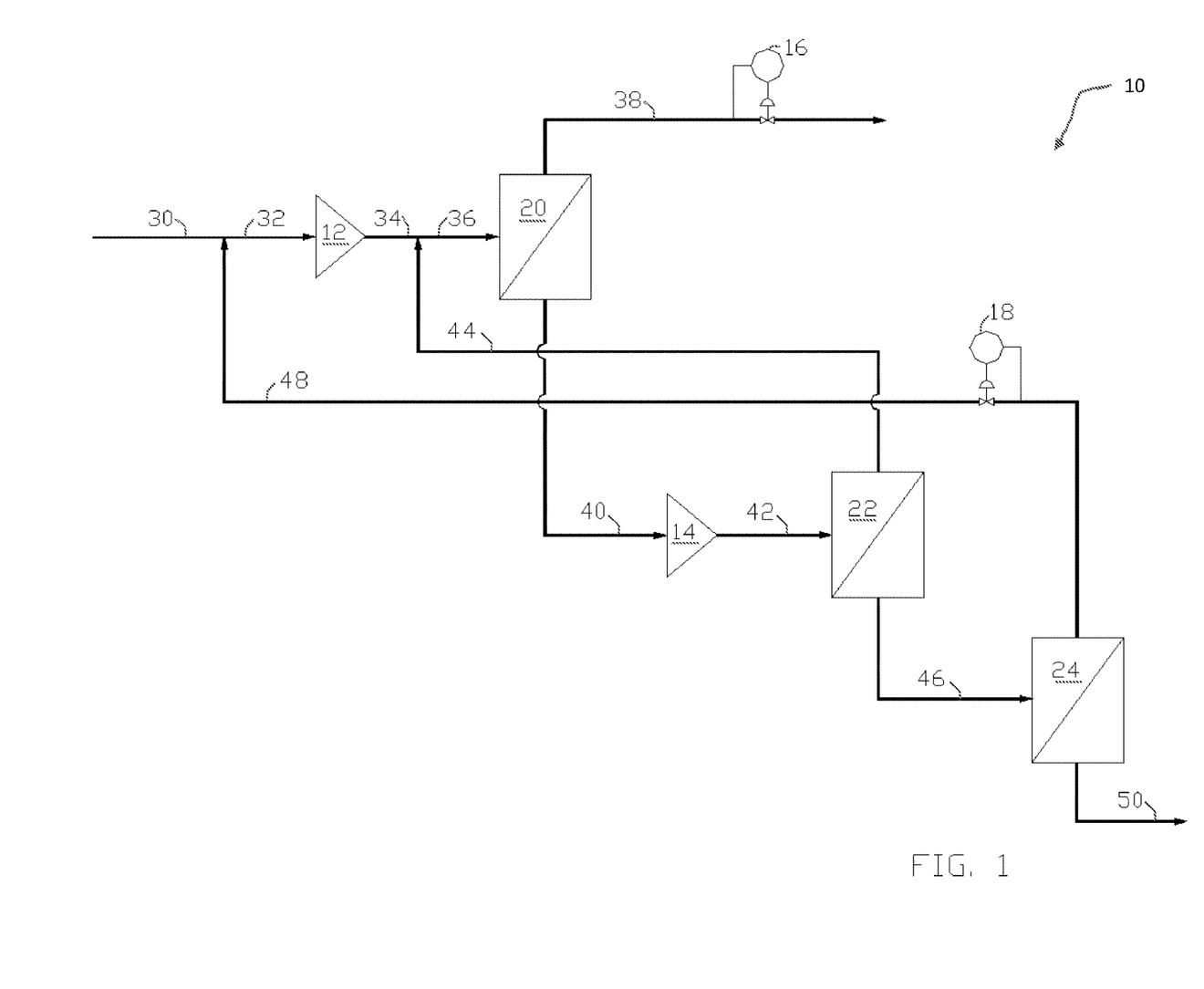
FIG. 1 is a process flow diagram of an embodiment of a three-stage membrane system and process using two compressors.

FIG. 1 shows an embodiment of a three-stage membrane biogas upgrading system 10 including two compressors. When used to upgrade or separate biogas, it can achieve at least 99.5% methane recovery. Biogas typically comprises carbon dioxide ($CO_2$) and methane ($CH_4$) as major constituents, sometimes along with other minor constituents such as oxygen ($O_2$) and nitrogen ($N_2$). Membranes used in the present system are selective for $CO_2$ over $CH_4$, meaning that $CO_2$ is considered a fast permeating gas that preferentially crosses the membrane at a relatively high rate while $CH_4$ is a slow permeating gas that crosses the membrane at a relatively low rate. As shorthand herein, a fast permeating gas and a slow permeating gas may be referred to a fast gas and a slow gas, respectively. Gas permeability through a membrane is governed by the solution-diffusion transport mechanism where the permeation rate is a function of the molecular size (diffusivity) and the molecular solubility in the polymer and is proportional to the driving force. The driving force for gas separation is the partial pressure differential between the high pressure and low pressure sides of the membrane. The gas permeability of each gaseous component of a gas mixture will typically be different, and the partial pressure of each gaseous component will obviously be proportional to its relative concentration in the gas mixture as well as the total pressure of the gas mixture.

Membranes have been used in gas separation process since the 1980s when Monsanto commercialized their PRISM® membrane for hydrogen purification. Since then, membranes have found uses in a variety of applications such as, but not limited to, natural gas sweetening, nitrogen production, and dehydration. More recently, membranes have been used in the growing field of biogas upgrading, supplanting traditional technologies such as amine scrubbing and water washing. Membranes offer many advantages over incumbent separation technologies such as reduced footprint, no moving parts, and no consumables or by-products needing additional treatment.

In the embodiment of FIG. 1, a raw feed gas stream 30 containing a mixture of a fast gas and a slow gas (e.g., biogas containing $CO_2$ and $CH_4$) is fed into the system 10. A first recycled stream 48 (also called a third nonpermeate stream 48, as discussed below) is mixed into the raw feed gas stream 30 to form a combined feed stream 32. The combined feed stream 32 is compressed to a higher pressure in a feed compressor 12 to yield a compressed combined feed stream 34. A second recycled stream 44 (also called a second nonpermeate stream 44, as discussed below) is mixed into the compressed combined feed stream 34 to form a pressurized feed gas stream 36.

The pressurized feed gas stream 36, containing a mixture of slow and fast permeating gases, is supplied to a first membrane stage 20 having a gas separation membrane that is selective for a fast gas over a slow gas. A control valve 16 (or other device that can maintain pressure, such as a restrictive orifice) is used to maintain appropriate pressure across the first membrane stage 20. In the case of biogas, $CO_2$ would permeate much more rapidly than $CH_4$. Gas comprising primarily fast gas plus a minority of slow gas permeates the membrane and exits the first membrane stage 20 as a first permeate stream 40, while gas comprising primarily slow gas plus a minority of fast gas that fails to permeate the membrane is rejected and withdrawn as a first nonpermeate stream 38. In the description herein, the terms retentate and nonpermeate may be used synonymously.

The first nonpermeate stream 38 can be withdrawn as a final product stream of the slow gas, having a high concentration of the slow gas and a very low concentration of the fast gas. The first permeate stream 40 is re-compressed in a first stage permeate compressor 14 (also called an inter-stage compressor), generating a compressed first permeate stream 42, i.e., a pressurized mixture of fast permeating gas with some amount of slow permeating gas, which is fed to a second membrane stage 22.

In the second membrane stage 22, gas comprising primarily fast gas plus a minority of slow gas permeates the membrane and exits the second membrane stage 22 as a second permeate stream 46, while gas comprising primarily slow gas plus a minority of fast gas which fails to permeate the membrane is rejected and withdrawn as the second nonpermeate stream 44. The second nonpermeate stream 44 remains pressurized since it failed to permeate the membrane and benefits from the recompression by the compressor 14. The second nonpermeate stream 44 is recycled back into the compressed combined feed stream 34 downstream of the feed compressor 12.

The second permeate stream 46 is fed to a third membrane stage 24 without any recompression. In the third membrane stage 24, gas comprising primarily fast gas plus a minority of slow gas permeates the membrane and exits the third membrane stage 24 as a third permeate stream 50, while gas comprising primarily slow gas plus a minority of fast gas fails to permeate the membrane is rejected and withdrawn as the third nonpermeate stream 48. The third nonpermeate stream 48 is recycled back into the raw feed gas stream 30 upstream of the feed compressor 12. A control valve 18 is used to maintain appropriate pressure across the third membrane stage 24. The third permeate stream 50 is a fast-gas rich stream, which in the case of biogas would be primarily $CO_2$, that can be vented or processed further depending on the application.

Optionally, a vacuum pump (not shown) can be connected to the first permeate stream 40 and/or the third permeate stream 50 to increase the differential pressure across the first stage or the third stage membrane respectively, which in turn improves the separating performance of the membrane stage.

Optionally, a process heater can be used upstream of any one of the membrane stages to increase the fast gas permeability and thus reduce the membrane area required. But the benefit is offset by a greater increase in the slow gas permeability which decreases the separating performance of the membrane stage.

In the system 10, each membrane stage 20, 22, and 24, may contain one or more membranes, with multiple membranes being arranged in series and/or parallel. Each membrane may be in the form of flat sheets or hollow fibers, and modules of membranes may be either a spiral wound flat sheet or a bundle of hollow fibers. It is not necessary for each membrane stage 20, 22, and 24 to use the same membranes. For example, in some embodiments, all three stages use membranes of the same permeability and selectivity. In other embodiments, the membrane permeability and selectivity of each stage may be different from that in the other stages. In yet other embodiments, two stages may use membranes of the same permeability and selectivity and the remaining stage may use membranes of a different permeability and selectivity. Each membrane may be made of a single polymer selected from the numerous polymers known in the art or future determined to be suitable for the desired separation, or each membrane may be a composite membrane made from multiple polymers. Examples of polymers used to make membranes include, but are not limited to, polystyrene, polysulfone, polyethersulfone, polyvinyl fluoride, polyvinylidene fluoride, polyether ether ketone, polycarbonate, polyphenylene oxide, polyethylene, polypropylene, cellulose acetate, polyimide (such as Matrimid 5218 or P-84), polyamide, polyvinyl alcohol, polyvinyl acetate, polyethylene oxide, polydimethylsiloxane, copolymers, block copolymers, or polymer blends.

Surprisingly, the use of the two compressors 12 and 14 in the system 10 drives high recovery of the slow gas with significantly lower compression costs than a more traditional 3-stage configuration that has a main feed gas compressor without additional compression, for example as in the prior art configuration of FIG. 6. Additionally, the configuration of the system 10 often leads to lower membrane area requirements, thereby reducing capital costs for the system.

Figure 2:
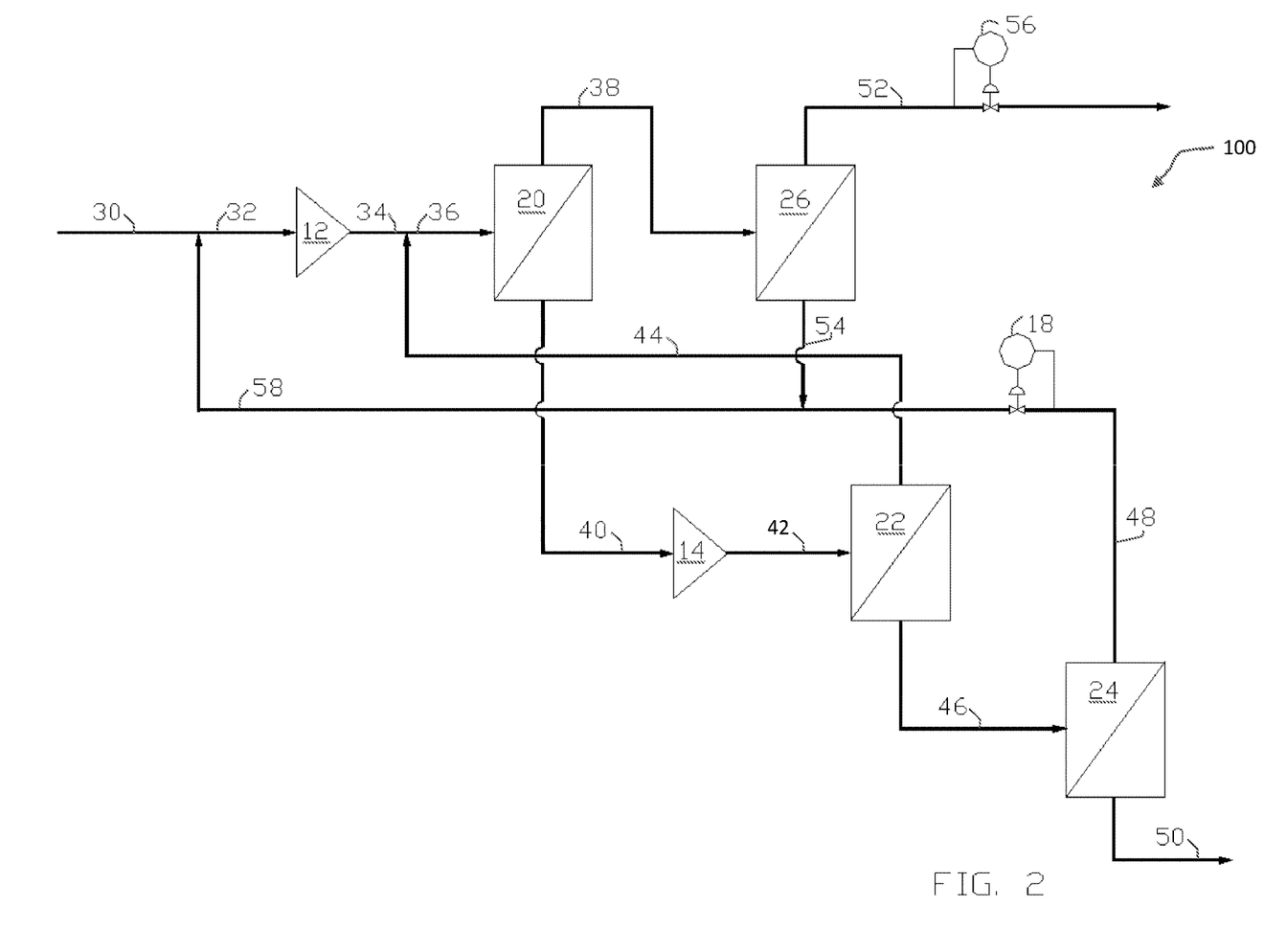
FIG. 2 is a process flow diagram of another embodiment of a four-stage membrane system and process using two compressors.

FIG. 2 shows another embodiment of a multi-stage membrane biogas upgrading system 100 including two compressors to obtain at least 99.5% methane recovery. In addition to the elements described above with respect to the system 10, the system 100 adds a fourth membrane stage 26 to further treat the first nonpermeate stream 38 rejected by the first membrane stage 20.

The first nonpermeate stream 38 is fed to the fourth membrane stage 26. In the fourth membrane stage 26, gas comprising primarily fast gas plus a minority of slow gas permeates the membrane and exits the fourth membrane stage 26 as a fourth permeate stream 54, while gas comprising primarily slow gas plus a very small fraction of fast gas fails to permeate the membrane is rejected and withdrawn as the fourth nonpermeate stream 52. The fourth permeate stream 54 combined with the third nonpermeate stream 48 to form a combined recycle stream 58 that is recycled back into the raw feed gas stream 30 upstream of the feed compressor. A control valve 56 is used to maintain appropriate pressure across the fourth membrane stage 26. The fourth nonpermeate stream 52 is a slow-gas rich stream, which in the case of biogas would be primarily $CH_4$, that exists the system 100 as a final purified product.

In both systems 10 and 100, for any given feed gas composition, flowrate requirements, and product requirements such as purity and/or recovery, the membrane areas in each stage are calculated from variables including, but not limited to, operating pressures, temperatures, and membrane type (i.e., membrane permeability and selectivity). These parameters are input into a computational simulation program such as Aspen Plus to find the optimal distribution of membrane area between the three or four stages, the flow rates and compositions of each respective recycle stream, and the direct impact of the recycle streams on compressor power.

The systems 10 and 100 described herein can be used to separate any one of several gas pairs in a feed stream 30, including, but not limited to: $CO_2/CH_4$, $H_2/CO$, $H_2/CO_2$, $CO_2/N_2$, $O_2/N_2$, $He/CH_4$, $H_2/CH_4$, and $H_2/N_2$.

Figure 3:
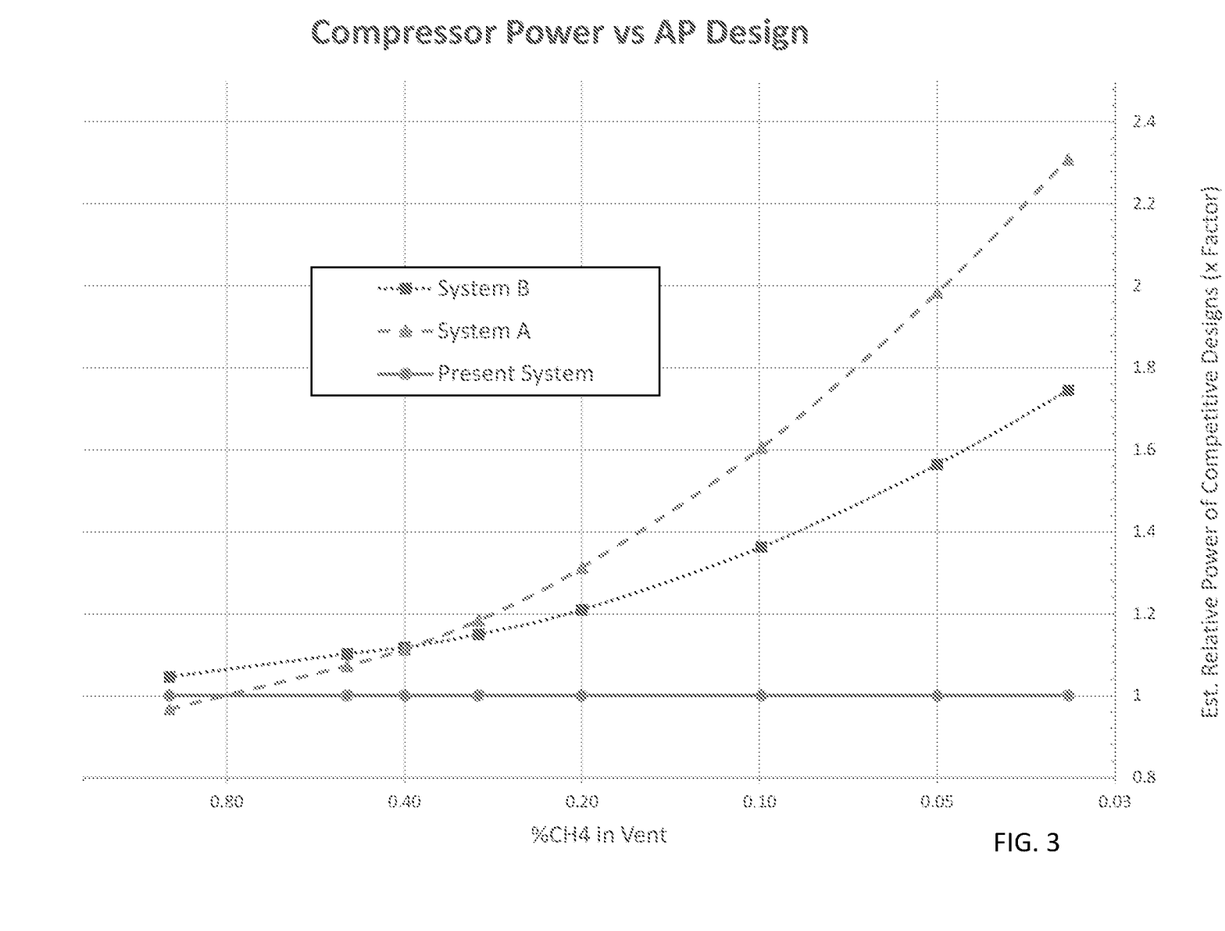
FIG. 3 is a graph comparing compressor power of prior art three-stage membrane configurations with a three-stage embodiment of the present invention.
Figure 4:
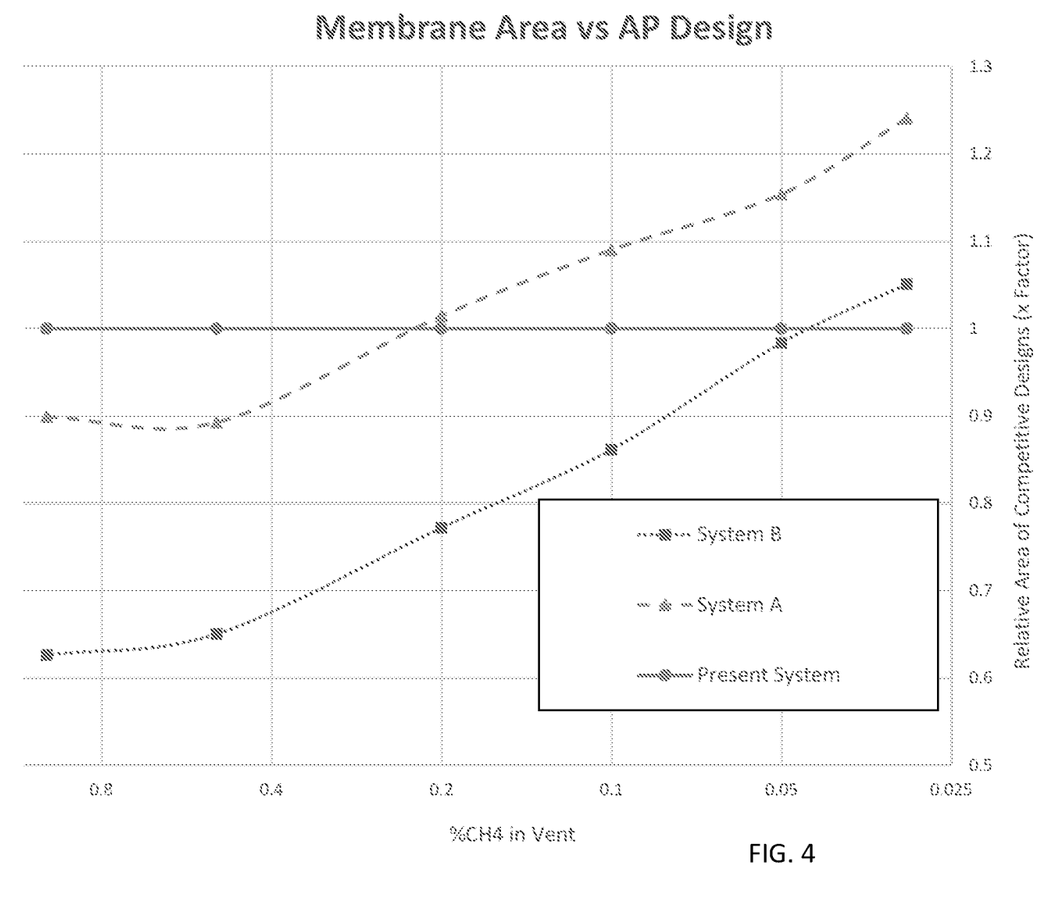
FIG. 4 is a graph comparing membrane area of prior art three-stage membrane configurations with a three-stage embodiment of the present invention.

The graphs of FIGS. 3 and 4, and the table below, compare the performance of the presently disclosed system 10 with the two prior art systems shown in FIG. 5 (System A) and FIG. 6 (System B). Simulations were performed using the following conditions: raw feed stream of 1000 NMH (normal cubic meters per hour) of biogas containing 60 mol % $CH_4$, 40 mol % $CO_2$, 14 barg operating pressure for the first and second stage membranes, 20° C. membrane operating temperature, product gas containing 98 mol % $CH_4$, membrane $CO_2/CH_4$ selectivity 30. As the graphs show, at more modest $CH_4$ recoveries (i.e., higher $CH_4$ content in the vent stream), the present system 10 with a three-stage cascade and two compressors performs similarly to Systems A and B. However, as the $CH_4$ recovery increases and the $CH_4$ in the vent stream decreases, the present system 10 requires significantly less compressor power than either System A (single compressor) or System B (two compressors). The present system also requires slightly less membrane area than single-compressor design of System A.

|  | Relative Membrane Area Required | Relative Required Compression Power |
|---|---|---|
| Present System 100 | 1 | 1 |
| System A (FIG. 5) | 1.15 | 1.98 |
| System B (FIG. 6) | 0.98 | 1.56 |

Conditions: 1000 NMH raw biogas at 60% $CH_4$, 40% $CO_2$, 14 barg, 20 C., product gas 98% $CH_4$, total $CH_4$ recovery 99.97%, membrane $CO_2/CH_4$ selectivity 30

A process simulation was performed using the configuration of FIG. 6, having three membranes and a single compressor, to generate a product stream containing 98 mol % $CH_4$ and an overall $CH_4$ recovery of 99.98% using a feed stream 30 containing 60 mol % $CH_4$ and 40 mol % $CO_2$ and flowing 1000 NMH. In order to achieve very high $CH_4$ recovery, above about 99.5%, a recycle ratio of over 500% is necessary, where the recycle ratio is defined as the ratio of the recycle stream volume (a combination of the streams labeled 7 and 8) to the feed stream volume (the stream labeled 1). This large recycle ratio would necessitate a very large compressor and would require excessively high compressor power to operate.

By comparison, a simulation was performed using the configuration of the system 10 having three membrane stages 20, 22, and 24 in cascade, a feed compressor 12, and a first stage permeate compressor 14. In the simulation, the membrane modules contained hollow fiber membranes having a CO2/CH4 selectivity of 30.

A feed of 1000 NMH of a raw biogas stream 30 containing 60% CH4 and 40% CO2 is provided to the system. The stream 30 is combined with the third nonpermeate stream 48 having a flow rate of 101.64 NMH and containing 96.5% CO2 to form the combined feed stream 32. The combined stream 32 is compressed to 14 barg. The resultant compressed combined feed stream 34 is combined with the second nonpermeate stream 44 at 842.8 NMH and containing 81.1% CO2 to create a pressurized feed gas stream 36 of 1944.4 NMH containing 39.3% CH4 and 60.7% CO2 at approximately 14 barg and 20° C. The compressed combined feed stream 36 is fed to the first membrane stage 20 to generate the first nonpermeate stream 38 and the first permeate stream 40.

The first membrane stage 20 contains 78.5% of the total membrane area in the system 10. The pressure of the first nonpermeate stream 38 pressure is regulated by a control valve 16, which is set to achieve a feed pressure of 14 barg to the first membrane stage 20. The first nonpermeate stream 38 had a molar flow rate of 611.9 NMH, contained 98% CH4, and is withdrawn as the product gas. The first permeate stream 40 had a molar flow rate of 1332.5 NMH entering the first permeate compressor 14.

The compressed first permeate stream 42 is fed to the second membrane stage 22 to generate the second nonpermeate stream 48 and the second permeate stream 46. The second membrane stage 22 contains 6.8% of the total system membrane area.

The second permeate stream 46 is fed to the third membrane stage 24, which contains 14.7% of the total system membrane area. The control valve 18 on the third stage nonpermeate stream 48 regulates the pressure on that stream, as well as the pressures of the third stage feed stream 46. The control valve 18 is set such that the pressure is sufficiently low so that a differential pressure is maintained across the second membrane stage 22 but high enough to maintain a differential pressure across third stage membrane 24. The optimum pressure can be determined by minimizing cost function using optimization routines, which allows that stream to be combined with the feed gas stream 34 leaving the feed compressor 12. As mentioned above, the volume of the third stage nonpermeate stream 48 is 101.6 NMH, and when recycled, this volume represents just a 10% increase in volume of gas to be compressed by the feed compressor 12. The third stage permeate stream 50 is withdrawn at 387.9 NMH and contains just 0.05 mol % CH4. Overall this system achieves 99.97% CH4 recovery while only using an estimated 0.286 kW/NMH raw biogas.

The presently described systems 10 and 100 represent an unexpected improvement over the single-compressor three-stage system of FIG. 6. Even though the system of FIG. 6 could be adapted to greater than 99.5% recovery by accepting higher recycle flows, using membranes with higher selectivity, and/or operating at a lower temperature to achieve higher selectivity, each of those has drawbacks compared with the presently described systems. Specifically, higher recycle flows require more compressor power, making the process less economical; membranes with higher selectivity are not currently available; and operating at lower temperatures to decrease selectivity increases refrigeration energy costs and increases membrane area.

The presently described systems 10 and 100 also represent an unexpected improvement over the two-compressor three-stage system of FIG. 5. Even though the system of FIG. 5 could be adapted to higher than 98% CH4 recovery, to achieve that high recovery, the ratio of permeate (second) stage feed flow to permeate flow ratio (known as the "stage cut") is reduced, which in turn reduces the permeate stage membrane area. At more than about 99% CH4 recovery, the permeate stage membrane area becomes so small that it becomes impractical to design and/or operate. Also, the ratio of permeate stage nonpermeate flow to feed stage permeate recycle flow increases, thereby increasing inter-stage compressor power consumption.

The present invention is not to be limited in scope by the specific aspects or embodiments disclosed in the examples which are intended as illustrations of a few aspects of the invention and any embodiments that are functionally equivalent are within the scope of this invention. Various modifications of the invention in addition to those shown and described herein will become apparent to those skilled in the art and are intended to fall within the scope of the appended claims.

The invention claimed is:

1. A method for separating a raw feed gas stream using a plurality of membrane separation stages, comprising:
feeding a pressurized feed gas stream to a first membrane stage;
separating the pressurized feed gas stream into a first nonpermeate stream and a first permeate stream;
compressing the first permeate stream in a first compressor to form a compressed first permeate stream;
feeding the compressed first permeate stream to a second membrane stage;
separating the compressed first permeate stream into a second nonpermeate stream and a second permeate stream;
feeding the second permeate stream into s third membrane stage;
separating the second permeate stream into a third nonpermeate stream and a third permeate stream;
combining the third nonpermeate stream with a raw feed gas stream to form a combined feed stream;
compressing the combined feed stream in a second compressor to form a compressed combined feed stream; and
combining the second nonpermeate stream with the compressed combined feed stream to form the pressurized feed gas stream.

2. The method of claim 1, further comprising:
withdrawing the first nonpermeate stream as a product gas stream.

3. The method of claim 1, further comprising:
withdrawing the third permeate stream as a waste gas stream.

4. The method of claim 1, further comprising:
controlling the pressure of the first nonpermeate stream; and
controlling the pressure of the third nonpermeate stream.

5. The method of claim 1, further comprising:
feeding the first nonpermeate stream into a fourth membrane stage;
separating the first nonpermeate stream into a fourth nonpermeate stream and a fourth permeate stream;

combining the fourth permeate stream with the third nonpermeate stream prior to combining the third nonpermeate stream with the raw feed gas stream to form the combined feed stream; and withdrawing the fourth nonpermeate stream as a product gas stream.

6. The method of claim 1, further comprising:

applying negative pressure to at least one of the first permeate stream and the third permeate stream.

7. A multi-stage membrane system for separating a raw feed gas stream, comprising:

a first membrane stage having a first feed port for receiving a pressurized raw feed gas stream, a first nonpermeate outlet for discharging a first nonpermeate stream, and a first permeate outlet for discharging a first permeate stream;

an interstage compressor having an interstage compressor inlet operatively connected to the first permeate outlet to receive the first permeate stream and an interstage compressor outlet for discharging a compressed first permeate stream;

a second membrane stage having a second feed port operatively connected to the interstage compressor outlet to receive the compressed first permeate stream, a second permeate outlet for discharging a second permeate stream, and a second nonpermeate outlet for discharging a second nonpermeate stream;

a third membrane stage having a third feed port operatively connected to the second permeate outlet to receive the second permeate stream, a third permeate outlet for discharging a third permeate stream, and a third nonpermeate outlet for discharging a third nonpermeate stream;

a first mixing junction having a raw feed gas inlet for receiving a raw feed gas stream, a first recycle inlet operatively connected to the third nonpermeate outlet to receive the third nonpermeate stream, and a first mixture outlet for discharging a combined feed stream consisting of a mixture of the raw feed gas stream and the third nonpermeate stream;

a feed compressor having a feed compressor inlet operatively connected to the first mixture outlet to receive the combined feed stream and a feed compressor outlet for discharging a compressed combined feed stream; and a second mixing junction having a combined feed inlet operatively connected to the feed compressor outlet to receive the compressed combined feed stream, a second recycle inlet operatively connected to the second nonpermeate outlet to receive the second nonpermeate stream, and a second mixture outlet operatively connected to the first feed port to supply the pressurized raw feed gas stream consisting of a mixture of the compressed combined feed stream and the second nonpermeate stream to the first membrane stage.

8. The system of claim 7, further comprising:

a fourth membrane stage having a fourth feed port operatively connected to the first nonpermeate outlet to receive the first nonpermeate stream, a fourth permeate outlet port for discharging a fourth permeate stream, and a fourth nonpermeate outlet for discharging a fourth nonpermeate stream;

wherein the fourth permeate stream is combined with the third nonpermeate stream prior to the third nonpermeate stream being received into the first mixing junction.

9. The system of claim 7, further comprising:

a first permeate vacuum pump to apply negative pressure to the first permeate outlet.

10. The system of claim 7, further comprising:

a third permeate vacuum pump to apply negative pressure to the third permeate outlet.

11. The system of claim 7, wherein the first membrane stage, the second membrane stage, and the third membrane stage each have membranes of the same permeability and selectivity.

12. The system of claim 7, wherein one of the first membrane stage, the second membrane stage, and the third membrane stage has membranes of different permeability and selectivity from the other two membrane stages.

13. The system of claim 7, wherein each of the first membrane stage, the second membrane stage, and the third membrane stage has membranes of different permeability and selectivity from each of the other membrane stages.

* * * * *